(12) United States Patent
Melbrod et al.

(10) Patent No.: US 8,733,648 B2
(45) Date of Patent: May 27, 2014

(54) SMART PHONE CASING AND INFORMATION EXCHANGE SYSTEM

(76) Inventors: Anastasia Melbrod, La Jolla, CA (US); Wesley Melbrod, Rancho Santa Fe, CA (US)

( * ) Notice: Subject to any disclaimer, the term of this patent is extended or adjusted under 35 U.S.C. 154(b) by 172 days.

(21) Appl. No.: 13/526,502

(22) Filed: Jun. 18, 2012

(65) Prior Publication Data

US 2013/0146661 A1 Jun. 13, 2013

Related U.S. Application Data

(60) Provisional application No. 61/498,498, filed on Jun. 17, 2011.

(51) Int. Cl.
*G06K 7/00* (2006.01)
*H04M 1/00* (2006.01)

(52) U.S. Cl.
USPC ........ 235/435; 235/380; 455/558; 455/556.2; 455/575.8; 455/575.1

(58) Field of Classification Search
USPC .............. 235/435, 380; 455/557, 558, 575.1, 455/575.8, 556.2
See application file for complete search history.

(56) References Cited

U.S. PATENT DOCUMENTS 8,355,670 B2 * 1/2013 White ........................ 455/41.1
2012/0122520 A1 * 5/2012 Phillips ..................... 455/556.2

* cited by examiner

*Primary Examiner* — Kristy A Haupt
(74) *Attorney, Agent, or Firm* — S McPherson IP Law

(57) ABSTRACT

The embodiments of the present invention relate to a smart phone casing and information exchange system which enables a user to carry a single system that merges the digital and telecommunications necessities of the individual with the personalized cards, membership accounts, consumer credit and/or medical insurance or health information in a single source protected both physically with a hardened case, and digitally with appropriate safeguards for electronic protection.

20 Claims, 7 Drawing Sheets

Figure 4
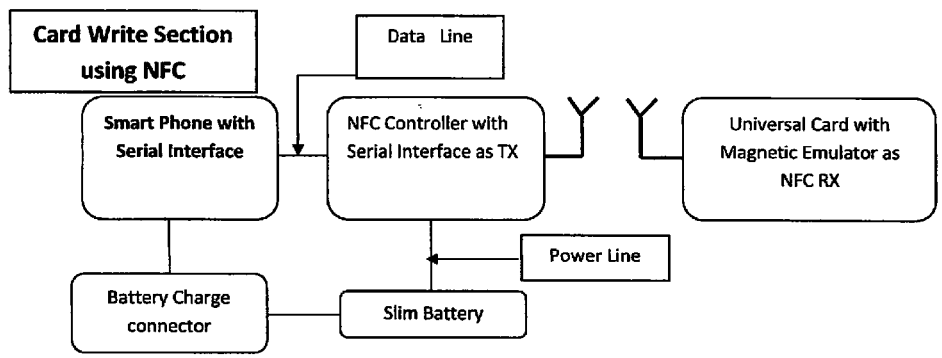
Fig. 4A
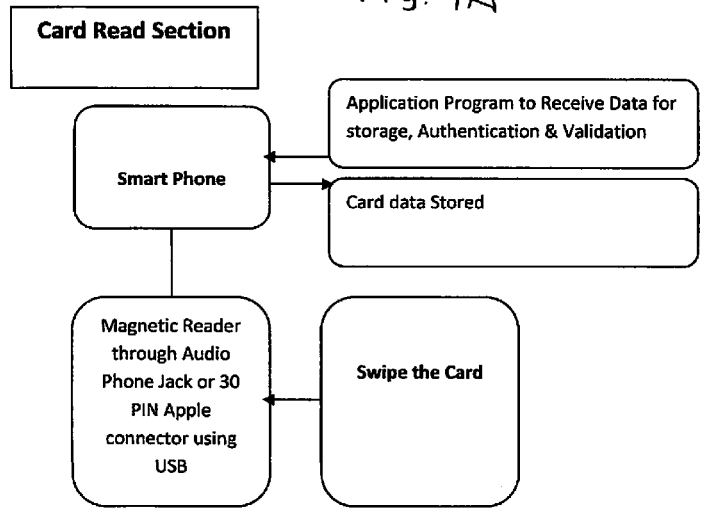
Fig. 4B

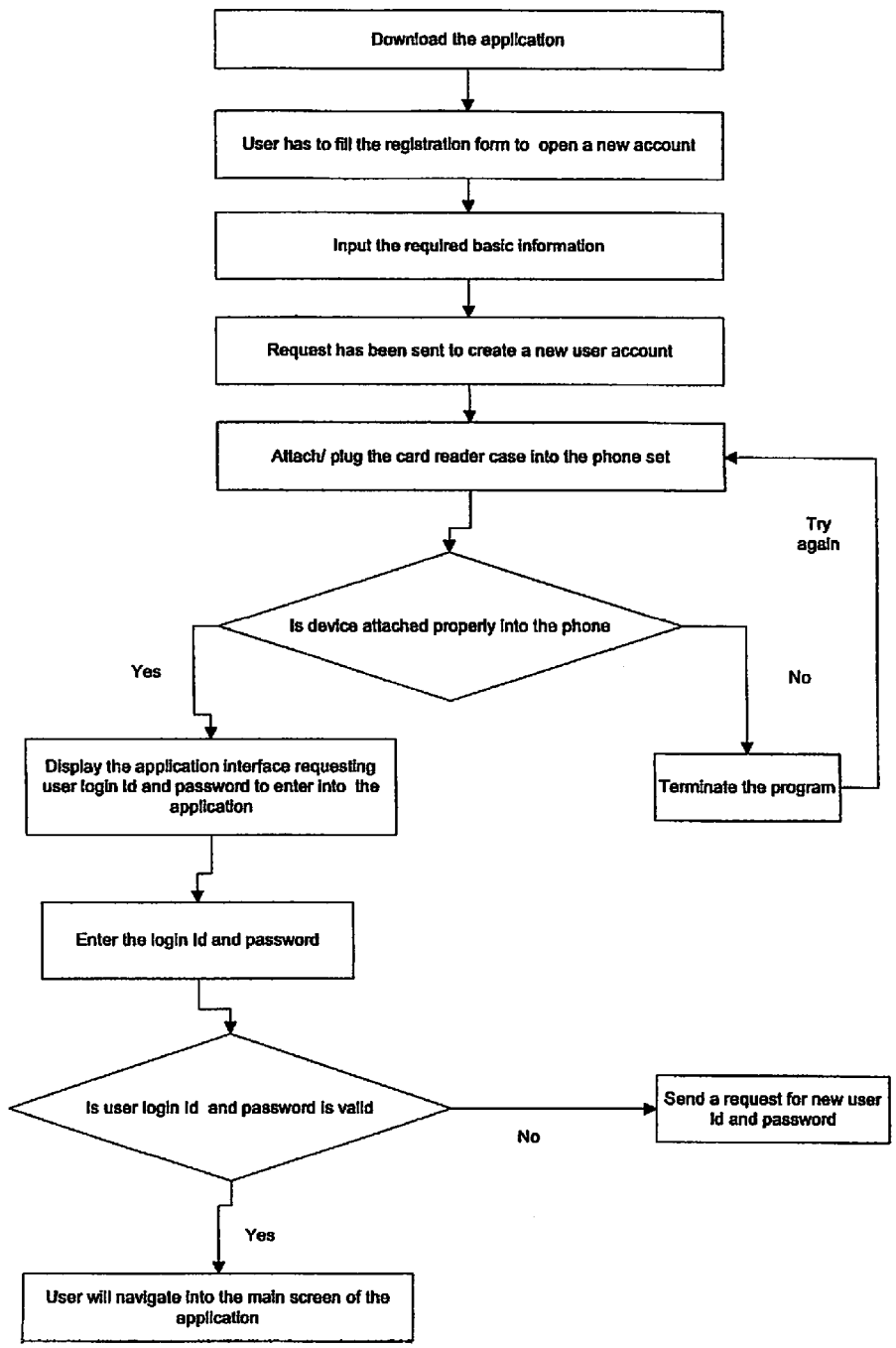

SMART PHONE CASING AND INFORMATION EXCHANGE SYSTEM

BACKGROUND OF THE INVENTION

1. Field of the Invention

The invention generally relates to a smart phone case enhanced with information exchange and digital wallet capabilities and more specifically to NFC electronic wallets with an NFC embedded detachable reconfigurable card.

2. Background Information

Smart phones and their protective cases are now a common utility needed to function in everyday life. People are now required to carry these smart phones along with wallets, purses, and handbags in order to have the information needed to go about a day. Currently a coordinated system which integrates this diversity of information with appropriate safeguards both physically and digitally does not exist in the prior art.

Traditionally, credit, loyalty, and personal information cards are insecure. In the event that the cards or information is lost, users are forced to immediately call each individual card issuer and have their cards canceled. The consumers must then wait several days to weeks for the replacement cards to be reissued and mailed.

Currently there are no smart-phone cases which allow consumers to simply logon to website and temporarily suspend all card use via the application with the click of a button, and then be able to purchase an additional case and reload the card information within hours.

Therefore, there is a need for a more secure device which enables a user to carry a single system that merges the digital and telecommunications necessities of the individual with the personalized cards, membership accounts, consumer credit and/or medical insurance or health information in a single source protected both physically with a case, a detachable card and digitally encrypted application that stores and transfers information. The system embodied in the present invention satisfies that need.

SUMMARY OF THE INVENTION

Embodiments of the present invention feature a device which enables a user to carry a single system that merges the digital and telecommunications necessities of the individual with the personalized cards, membership accounts, consumer credit and/or medical insurance or health information in a single source which is protected both physically with a hardened case that houses a detachable card, and digitally through an encrypted application used to receive, store, and transfer information.

One embodied smart phone casing and information exchange system comprises a protective smart phone outer casing; a universal transaction card and an application downloaded onto a smartphone. The smart phone casing is made of rigid materials capable of providing physical protection of the smart phone from damage. The casing further comprises of a chip and/or data storage device which interacts physically or wirelessly with the smart phone; a slot for storing said universal card, and a universal card writer. The embodied universal transaction card comprises an information storage function which enables the card to be loaded with information necessary to complete a desired information exchange. The embodied information exchange system further includes an application or "App" which comprises of digital safeguards for preserving sensitive information and the capability to interface with the chip writer to program said universal card to provide information for a specific information exchange transaction.

Additional embodiments include a card reader portion within the casing.

Additional embodiments of the invention related to the universal transaction card includes a magnetic stripe card emulation for storing users' payment and loyalty cards.

Yet additional embodiments for the universal card include security features wherein the universal card is demagnetized thus rendering the card unreadable after any of the following; a programmed number of uses; a set amount of time; or the application is prompted to lock-out further uses of the card until the card is reprogrammed.

Additional embodiments include a casing with of an imbedded NFC chip used to communicate and transfer information to the universal transaction card wherein said information storage function is performed with an NFC imbedded smart card and wherein the NFC imbedded smart card may have an integrated circuit which communicates with said NFC chip through an imbedded NFC antenna.

Another embodied smart phone casing and information exchange system comprises of a protective smart phone outer casing; a universal transaction card and an application downloaded onto a smartphone. The casing is made of rigid materials capable of providing physical protection of a smart phone from damage, the casing additionally comprises of a NFC chip and/or data storage device which interacts wirelessly with the smart phone, a slot for storing said universal card, and a universal card writer and wherein said universal transaction card comprises an information storage function which enables the card to be loaded with information necessary to complete a desired information exchange. The universal transaction card comprises of a magnetic stripe card emulation for storing users' payment and loyalty cards wherein said application comprises of password protective logins and identification codes for preserving sensitive information and the capability to interface with the chip writer to program said universal card to provide information for a specific information exchange transaction. The embodied application further comprises a security feature which allows for the remote login from an alternate computing source to allow for access to said information exchange either by providing further account information or for disabling the ability to use or view the information should the system become lost or stolen.

Yet another embodied smart phone casing and information exchange system comprises a protective smart phone outer casing; a universal transaction card and an application downloaded onto a smartphone as described above. The smart phone casing comprises of a NFC chip and/or data storage device which interacts physically with the smart phone; a slot for storing said universal card, and a universal card writer; wherein said universal transaction card comprises an information storage function which enables the card to be loaded with information necessary to complete a desired information exchange; and wherein said universal transaction card comprises of a NFC smartcard with a magnetic stripe card emulation for storing users' payment and loyalty cards. The embodied "app" comprises of password protective logins and identification codes for preserving sensitive information and the capability to interface with the chip writer to program said universal card to provide information for a specific information exchange transaction. The application further comprises a remote login from an alternate computing source to allow for access to the information exchange either by providing further account information or for disabling the ability to use or view the information should the system become lost or stolen.

Additional embodiments include physical connections from the case to the phone selected from one of the following connection possibilities: 30 point pin connection, USB, Micro USB, and audio jack. With 30 point pin connection, and microUSB most preferred.

The phone application will communicate information via the NFC (Near Field Communication) embedded case to a secure NFC embedded smart card that will emulate card information.

BRIEF DESCRIPTION OF THE DRAWINGS

The principles of the present invention will be apparent with reference to the following drawings, in which like reference numerals denote like components:

FIG. 4 consists of FIGS. 4A and 4B which show the flow diagrams of a card write section using an NFC writer and a card read section respectively.

FIG. 5 is a Task flow diagram for an example of a new user account creation and an account verification process.

DETAILED DESCRIPTION OF THE INVENTION

Definitions

Figure 1:
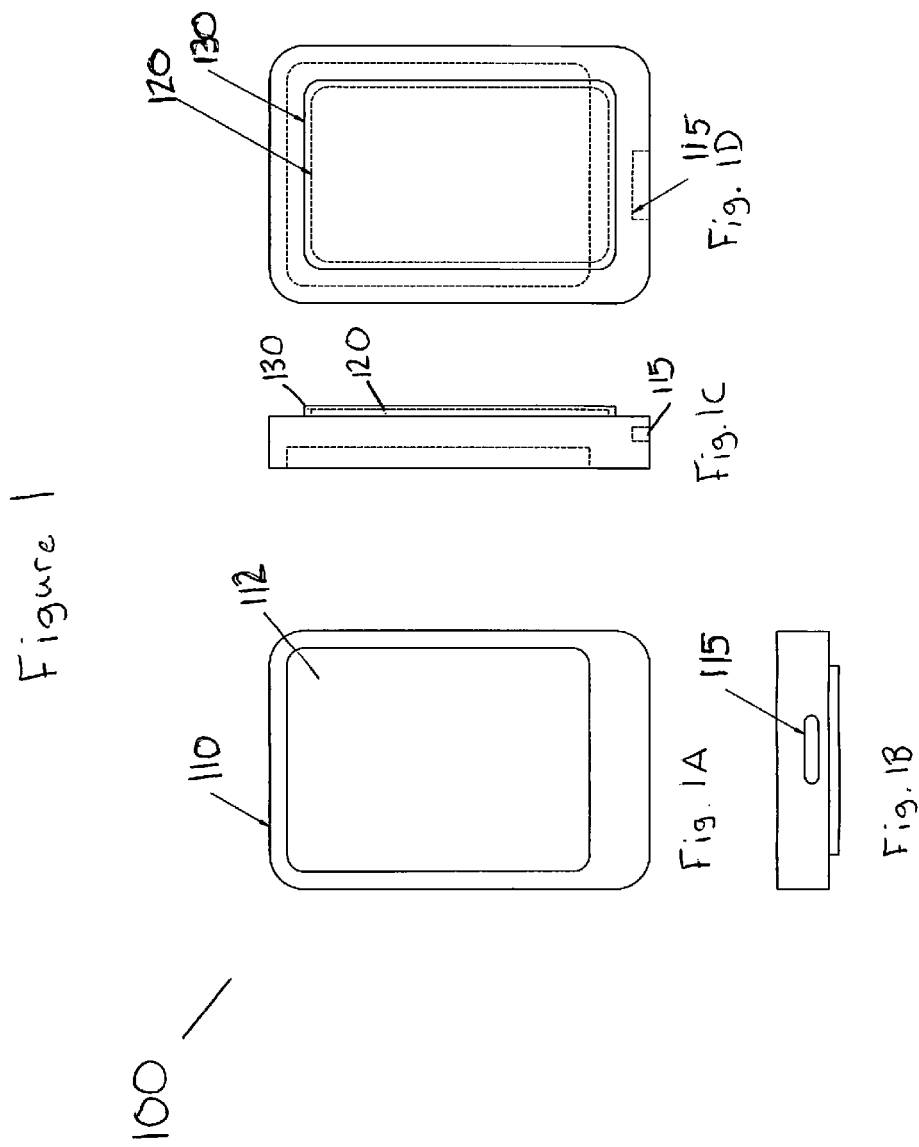
FIG. 1 consists of FIGS. 1A through 1D and comprise of various views a of an embodied case of the present invention when viewed from the front FIG. 1A, the bottom FIG. 1B, the side FIG. 1C and the back FIG. 1D.

For the purpose of the present invention a "smart phone" is defined as a mobile phone that is built on a mobile computing platform, with more advanced computing ability than a feature phone. Smart phones computing offers a wide range of functions through the use of downloadable Apps.

For the purpose of the present invention an "App" is a software application that is designed to run on a smartphone. They are available through application distribution platforms, which are typically operated by the owner of mobile operating system, such as Apple App Store, Google Play, Windows Phone Market Place and Blackberry App World.

For the purpose of the present invention a "protective case" is a plastic or rubber coating used to seal and protect both the external and internal components of a smart phone.

For the purpose of the present invention a "universal card" is a single card that is capable of serving the function of multiple cards. (E.g. Bank cards, loyalty cards, gift cards, credit cards) The card contains an internal memory that allows it to store card information for specific periods of time and or number of uses, as dictated by the user. This memory is programmed by the card user through an application that communicates with the card through NFC.

For the purpose of the present invention a "payment card" is a card backed by either a credit, debit card, charge card, or gift card. Payment Cards are traditionally presented at a point of sale terminal where a merchant will swipe the cards magnetic strip through a magnetic reader that processes card data.

For the purpose of the present invention a "loyalty card" is a structured marketing effort that rewards consumers for loyalty buying history. By using Loyalty Cards, consumers receive discounts, gifts, and other incentives for repeated spending.

For the purpose of the present invention an "NFC imbedded smart card" is a card that houses an integrated circuit which communicates to an external device through an imbedded NFC antenna.

For the purpose of the present invention a "NFC case" is a protective case that houses a NFC Chip used to communicate with an external device.

The present invention is based on a smart phone case enhanced with information exchange and digital wallet capabilities and more specifically to NFC electronic wallets with an NFC embedded detachable reconfigurable card.

Embodiments of the present invention feature a mechanism which enables a user to carry a single system that merges the digital and telecommunications necessities of the individual with the personalized cards, membership accounts, consumer credit and/or medical insurance or health information in a single source protected both physically with a hardened case, a detachable card and digitally encrypted application that receives, stores, and transfers information.

The amount of smartphone users that currently utilize a "protective case" is predominantly high. The present invention can serve as a digital wallet that uses an NFC phone case and NFC imbedded smart card that emulates magnetic strip information. The embodied case and card device allows consumers to remove the dozens of plastic cards typically carried and replace them with one digitally secured universal smart card.

Additional embodiments feature personalized offering systems such as coupons and promotional deals and certificates such as "Groupon" and the like. These offering systems are improved by the present invention by allowing consumers to securely store the offerings and be rid of the traditional coupon redemption experience.

Additional embodiments appeal to merchants: who wish to provide digital incentives and want to incentivize them by having some sort of offer in the store with an embodied system. The embodied app exclusive data collected will assist in driving the offer, so matching up the transaction data, preference data, location-based data, and the preference of friends, reviews and ratings, will create a way to personalize and market to those specific customers that they want, their more preferred/profitable consumer base.

Additional embodiment apps may integrate with social networks. These embodiments add value in that the technology itself includes features and functions that are most enticing for consumers are simple yet comprehensive. An embodiment with advantages on the merchant side include the fact that going digital is a cleaner/greener technology which will assist with corporate sustainability efforts.

Embodiments of the invention integrate the currently utilized magnetic stripe card technology into an encrypted application that allows for higher levels of security and greater consumer convenience.

Additional embodiments feature a sleek yet protective case which includes a removable card that emulate magnetic the stripe information of the various cards that are stored on the application. The application reflects the consumers choice of cards and gives consumers options regarding how often they would like that information cleared. The security embodied apps and the device itself, provide protection against fraud and/or if a consumer has lost his or her phone and an embodied case was attached to it consumers may easily access and lock their account through a remote online login.

Additional security protections include the ability to completely erase the data on a card as soon as the card is placed back in the case post purchase. When the data is completely erased, the user is required to log back into the app to choose a new method of payment or to reactivate the card with the previously stored information.

Additional advantages of embodiments of the present invention are that it is very versatile and can be all inclusive because it is attached to the smartphone of a users choice. The consumer need only find the right model of the embodied case and systems for their phone, download the app and have the contents of their wallet ready to use by payment processing vendors and/or personal records availability for medical offices and or government agencies.

Additional embodiments of the present invention feature a shielded casing which has the capacity to reduce user exposure to electromagnetic fields and radiation associated with wireless phone use.

The components of an embodied devices may include: NFC imbedded cases which communicate with an NFC imbedded card that has built in magnetic emulating technology.

The contemplated hardware may be connected from case to phone via, 30 point pin connection, USB, Micro USB, and audio jack connections.

Exemplary components include NFC/RFID chips, NFC bridge devices, and flex antennae embedded within the case:

The bridge devices may include NFC that can interact with currently available quick pay NFC checkout technology.

Smart cards which are capable of storing, retrieving, and emulating data are embodiments of the present invention.

Embodiments will include a NFC imbedded card which emulates magnetic stripe information. The Magnetic emulating card will communicate with the case via NFC and/or UI software applications. User may choose how often the card data will change as dictated in user settings. Through the Magnetic Stripe Card emulation: the universal transaction card is programmed to act as the users' credit, debit, loyalty, transit, or any other information carrying card. The card can be made to demagnetize as dictated by the user (such as after each purchase, after 5 purchases, only when a new card is selected; or after a set period of time 1 minute after programming, 5 minutes after programming, 1 hour after programming).

The embodied cases are designed to store the NFC card in a location that precisely aligns it with the NFC chip imbedded in the case. This alignment which may be achieved through a tracking or slot means places the two communication points in the optimal location to allow for consistent connection and transferring of data.

The embodied software and/or Apps comprises of a user interface to receive, store, and transmit card information. The embodiments of the contemplated App serve as the digital wallet, with all-encompassing security, with the ability to send information to the Dynamic magnetic stripe, along with read barcodes, and use the NFC/RFID technologies, and serve as a one stop shop for a person to store all of the information currently carried around in their wallet. The app may require a user to log into the app and enter their PIN, similar to that in use with ATMs currently, this ensures if the phone is lost or stolen, the app could not be entered without knowing this code. An additional security feature within the app, includes the ability to clear the data from the card if it is lost or stolen, either by reporting the card as lost or remotely from a computer or other smart phone source. So a user could go on their computer and note that their phone was lost or stolen and with the entering of another secure PIN, they could clear their data from the card and/or app.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

FIG. 1 comprising FIGS. 1A, 1B, 1C and 1D show an embodied case contemplated in the present invention. The side view shows where a contemplated hotel key type magnetic card will engage and disengage with the system when being swiped or scanned at a point of service interaction. FIG. 1A shows the front view of an embodied system 100 and its accompanying case 110. A window for a smartphone screen is shown in 112. FIG. 1B shows the bottom surface of the embodied case 110 and the accompanying physical interface of the case with the phone as represented by a female USB jack 115. FIG. 1C shows a side view of the embodied case 110 in which the card storage area 130 is viewable and an outline of a universal card 120 is present the relationship of the USB jack 115 is also shown at the bottom. FIG. 1D is a backside view of the device showing placement of the card storage 130 and universal card 120 on the case 110.

Figure 2:
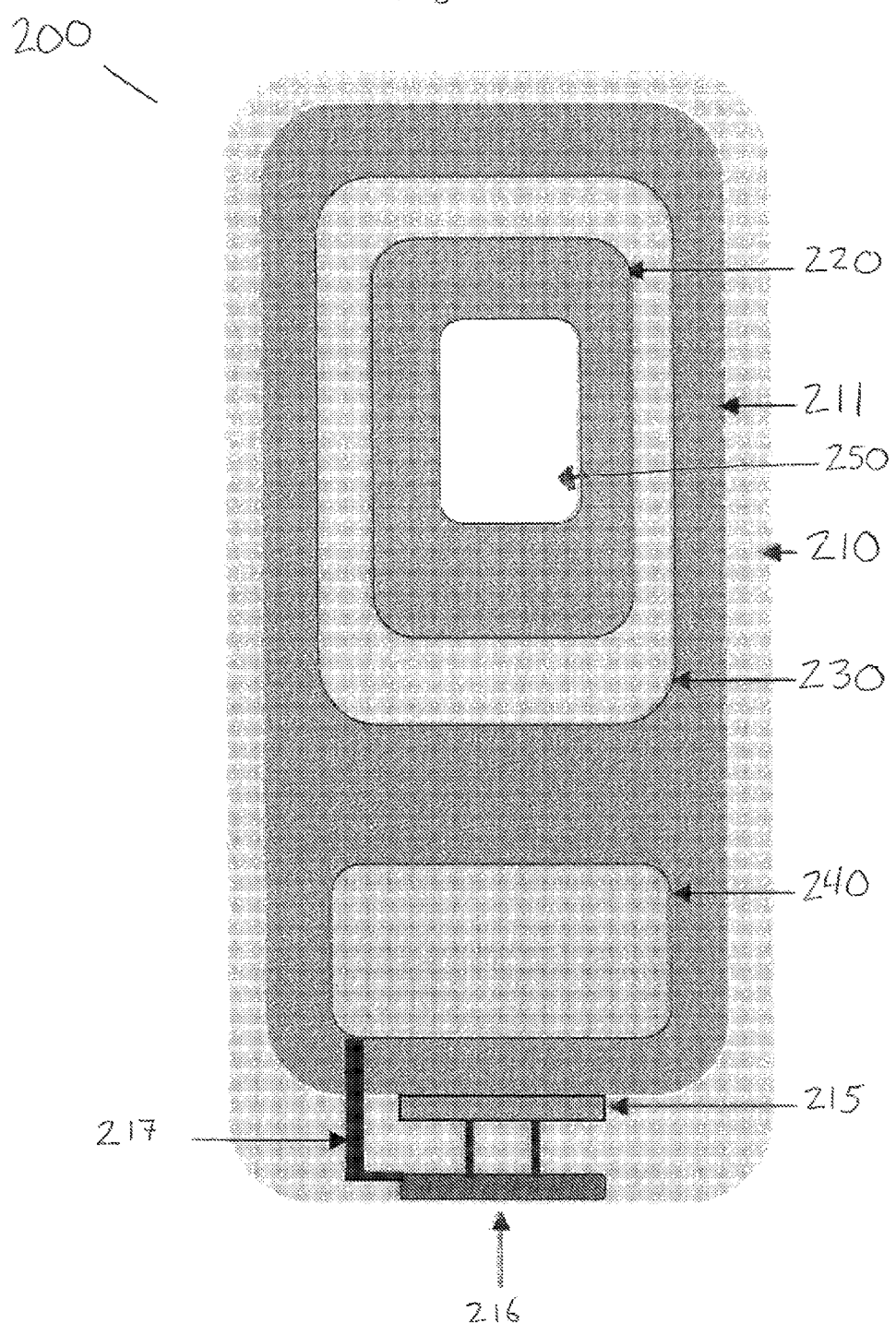
FIG. 2 is a front plan view of another embodied case with cut aways to show the various internal features imbedded within the case.

Another embodied smart case and communication system 200 of the present invention is shown in FIG. 2. The case 210 surrounds the smartphone 211 and is physically connected to the phone for data transfer line 217 which is created through the interface of the smart case 110 Apple 30 pin male connector 216 which connects with the Apple 20 pin female connection 215 on the smartphone 211. Additionally the position of the universal card 220 is shown within the card holder 230 and with and embedded NFC chip 250. The NFC writing controller component 240 is visible as well.

Figure 3:
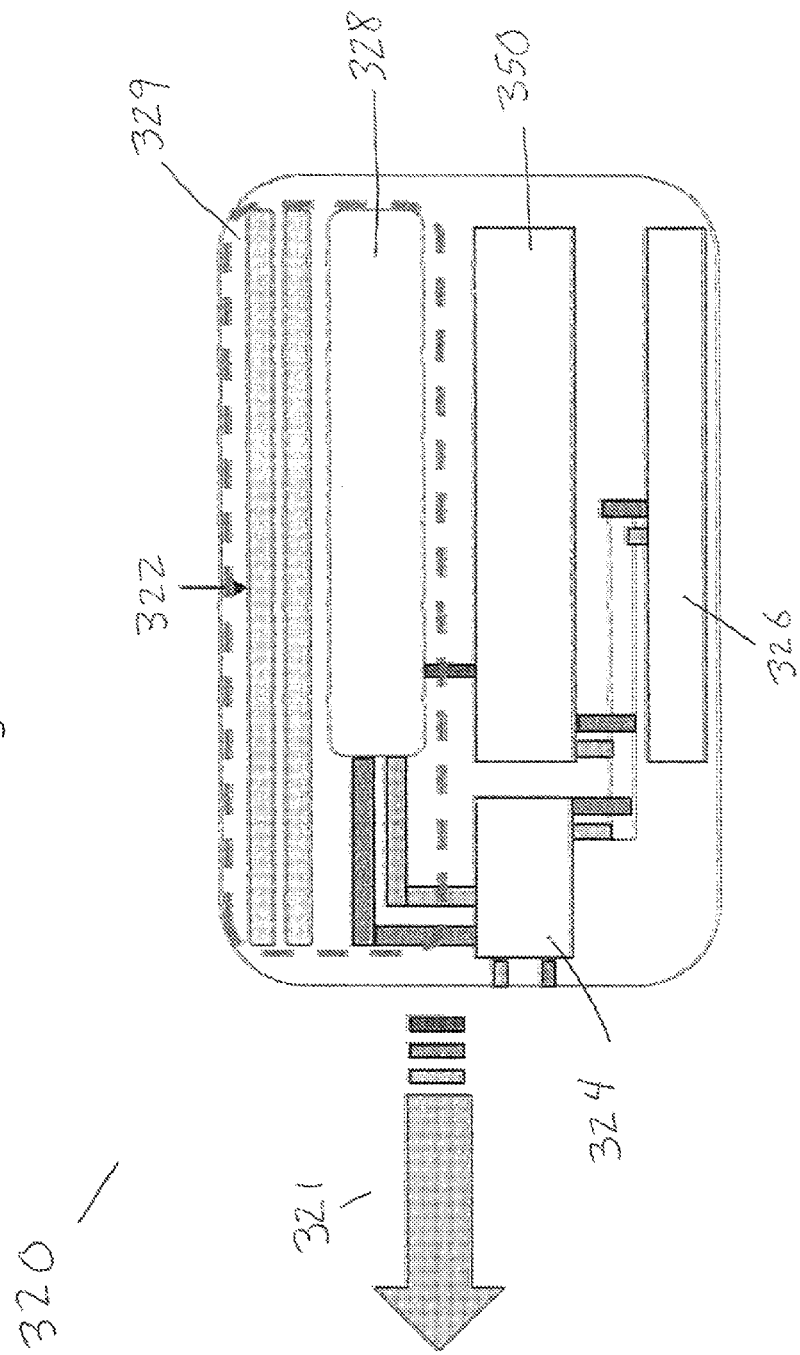
FIG. 3 is a front plan view of an embodied universal card with cut aways to show the various internal features imbedded within the card.

An embodied universal transaction card 320 is shown in FIG. 3. The features viewable in this cut away include the direction to smart case 321 and the card alignment track 322 which helps ensure the proper orientation of the NFC components between the case (not shown) and the card 320 within the card lab technology zone 329. A power source 324 such as a battery may be included within the card 320. Additional features include a Wake-up circuit interface 326 and a contactless writing NFC chip 350 which interfaces with the magnetic emulating circuit 328 to provide the card 320 with the data required for the programmed transaction.

FIG. 4 includes FIGS. 4A and 4B. FIG. 4A represents a flow diagram of a card write section using NFC contemplated in the present invention. A smart phone with a serial interface has a data in to provided the NFC controller with the serial interface as TX, this interaction then mated with the Universal Card with a Magnetic Emulator as the NFC RX. FIG. 4B represents a flow diagram of a Card read section wherein the Application Program to Receive Data for storage, authentication a validation is loaded on a smartphone. A card is swiped in the case and the magnetic reader provides the information to the smartphone through one of the listed connectors and the card data is stored.

Example 1—Process for Creating a New User Account and Account Verification

FIG. 5 exemplifies a Task flow diagram for an example of a new user account creation and an account verification process comprising the following steps:
- A) The application is downloaded onto the smart phone.
- B) The user completes the user registration form to open a new account.
- C) The user inputs the required information.
- D) A request is sent to create a new user account. Once the request for the new user account is verified the user may attach or plug the card reader case into the phone set.
- E) A check is provided to determine whether the device is attached properly into the phone if it is not the program is terminated. If it is attached properly a display of the application interface requesting user login ID and password to enter the application is shown.
- F) The user enters their login ID and password.
- G) A check is provided to determine if the user login ID and password is valid, if it is not the program is terminated or a request for a new user ID and password is generated. If the login and password are determined to be valid the user navigates into the main screen of the application.

Example 2—Card Reading Process

Figure 6:
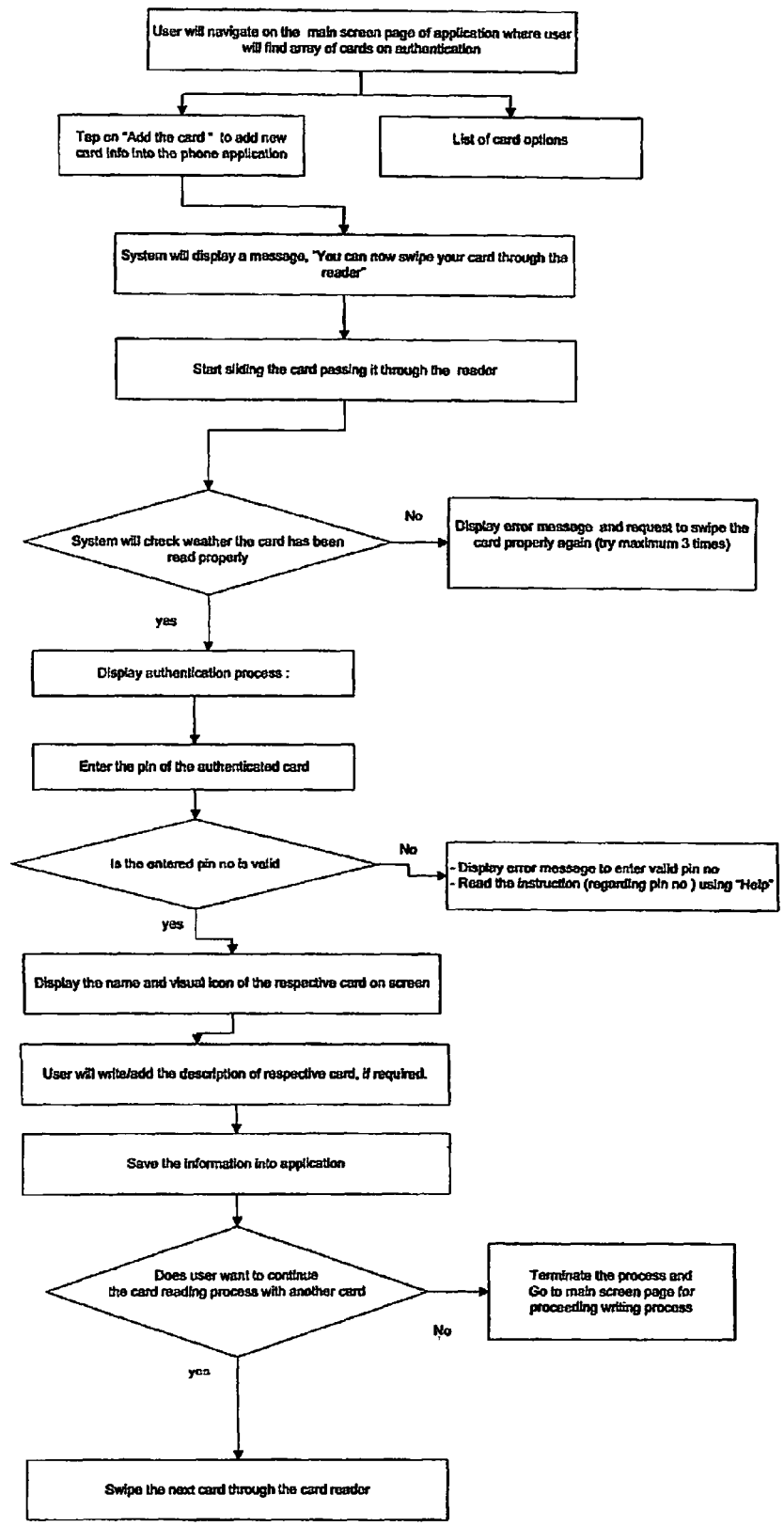
FIG. 6 is a Task flow diagram for an exemplary card reading process.

FIG. 6 exemplifies a Task flow diagram for an exemplary card reading process comprising the following steps:
- A) The user navigates on the main screen page of the application to the site where the user will find the array of cards listed on authentication.
- B) The user Taps on "add the card" to add the new card information into the phone application or to review a list of card options.
- C) The system displays a message such as "You can swipe your card through the reader."
- D) The user slides the card passing it through the reader.
- E) The system checks whether the card has been properly swiped and/or read, if it has not an error message is displayed and a request to swipe the card properly again is presented, with a default maximum number of swipe attempts allowed (such as 3) before program terminates. If the card has been swiped properly a display of the authentication process will begin.
- F) The user enters a pin number and/or other security information, and the system determines whether the security clearance via the pin number, etc is correct. If the security information is incorrect a display error message is provided and a request to enter valid information e.g., a valid pin number is shown.
- G) Optionally there may be an instruction regarding "Help" for questions or problems with identifying or inputting the correct pin number. For example if the pin number is forgotten there may be a way to retrieve the pin number through proper authentication and the code may be sent to an email address.
- H) If the user enters the pin number and/or other security information and the system determines that the information is correct or valid a display of the name and card icon of the respective card is presented on the screen.
- I) The user writes or adds a description for the respective card if required and the information is saved into the application.
- J) The user is then prompted to either terminate the process and go to the main page to proceed with the writing process or add another card into the system by swiping the next card through the card reader.

Example 3—Card Writing Process

Figure 7:
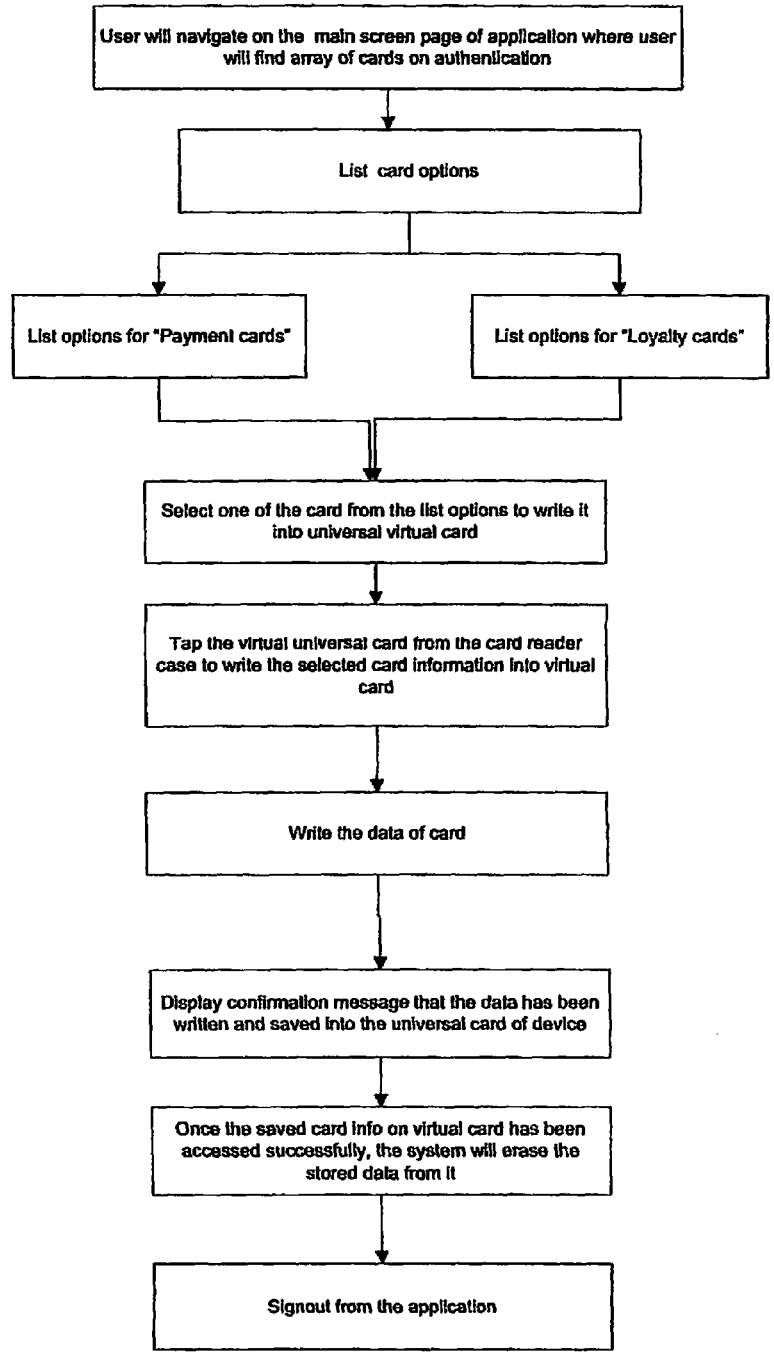
FIG. 7 is a Task flow diagram for an exemplary card writing process.

FIG. 7 exemplifies a Task flow diagram for an exemplary card writing process comprising the following steps:
- A) The user navigates on the main screen page of the application which of the cards the user would wish to use after authentication is verified.
- B) A list of card options is provided such as Payment cards, Loyalty cards or Identification cards.
- C) One card from the list is selected to write it onto the universal virtual card.
- D) The user taps the virtual universal card from the card reader case to write the selected card information into the virtual card.
- E) The data is written onto the card.
- F) A confirmation message is displayed that the data has been written and saved into the universal card of device.
- G) Once the saved card information has been accessed successfully, the system may be programmed to erase the stored data from it.
- H) The user then signs out of the application or an automatic signoff occurs once the card is restored to the case.

Although the invention has been described with reference to the above example, it will be understood that modifications and variations are encompassed within the spirit and scope of the invention. Accordingly, the invention is limited only by the following claims.

What is claimed is:

1. A smart phone casing and information exchange system which comprises:
   - i. a protective smart phone outer casing; a universal transaction card and an application downloaded onto a smartphone;
   - ii. wherein said smart phone casing is made of rigid materials capable of providing physical protection of a smart phone from damage, and said casing further comprises of a chip and/or data storage device which interacts physically or wirelessly with the smart phone; a slot for storing said universal card, and a universal card writer;
   - iii. wherein said universal transaction card comprises an information storage function which enables the card to be loaded with information necessary to complete a desired information exchange; and
   - iv. wherein said application comprises of digital safeguards for preserving sensitive information and the capability to interface with the chip writer to program said universal card to provide information for a specific information exchange transaction.

2. The casing and exchange system of claim 1, wherein said smart phone casing further comprises a card reader.

3. The casing and exchange system of claim 1, wherein said universal transaction card comprises a magnetic stripe card emulation for storing users' payment and loyalty cards.

4. The casing and exchange system of claim 3, wherein said universal card is demagnetized thus rendering the card unreadable after any of the following; a programmed number of uses; a set amount of time; or the application is prompted to lock-out further uses of the card until the card is reprogrammed.

5. The casing and exchange system of claim 3, wherein said programmed number of uses is 3 to 5.

6. The casing and exchange system of claim 3, wherein said programmed number of uses is after each single use.

7. The casing and exchange system of claim 3, wherein said set amount of time before the card is timed out rendering the card unusable until being reprogrammed is between 1 minute and 1 hour.

8. The casing and exchange system of claim 1, wherein said application further comprises a remote login from an alternate computing source to allow for access to said information exchange either by providing further account information or for disabling the ability to use or view the information should the system become lost or stolen.

9. The casing and exchange system of claim 1, wherein the casing further comprises of an imbedded NFC chip used to communicate and transfer information to the universal transaction card wherein said information storage function is performed with an NFC imbedded smart card.

10. The casing and exchange system of claim 1, wherein the NFC imbedded smart card comprises an integrated circuit which communicates with said NFC chip through an imbedded NFC antenna.

11. A smart phone casing and information exchange system which comprises:
  i. a protective smart phone outer casing; a universal transaction card and an application downloaded onto a smartphone;
  ii. wherein said smart phone casing is made of rigid materials capable of providing physical protection of a smart phone from damage, and said casing further comprises of a NFC chip and/or data storage device which interacts wirelessly with the smart phone; a slot for storing said universal card, and a universal card writer;
  iii. wherein said universal transaction card comprises an information storage function which enables the card to be loaded with information necessary to complete a desired information exchange;
  iv. wherein said universal transaction card comprises a magnetic stripe card emulation for storing users' payment and loyalty cards;
  v. wherein said application comprises of password protective logins and identification codes for preserving sensitive information and the capability to interface with the chip writer to program said universal card to provide information for a specific information exchange transaction; and
  vi. wherein said application further comprises a remote login from an alternate computing source to allow for access to said information exchange either by providing further account information or for disabling the ability to use or view the information should the system become lost or stolen.

12. The casing and exchange system of claim 11, wherein said universal card is demagnetized thus rendering the card unreadable after a programmed number of uses.

13. The casing and exchange system of claim 12, wherein said programmed number of uses is 3 to 5.

14. The casing and exchange system of claim 12, wherein said programmed number of uses is after each single use.

15. A smart phone casing and information exchange system which comprises:
  i. a protective smart phone outer casing; a universal transaction card and an application downloaded onto a smartphone;
  ii. wherein said smart phone casing is made of rigid materials capable of providing physical protection of a smart phone from damage, and said casing further comprises of a NFC chip and/or data storage device which interacts physically with the smart phone; a slot for storing said universal card, and a universal card writer;
  iii. wherein said universal transaction card comprises an information storage function which enables the card to be loaded with information necessary to complete a desired information exchange;
  iv. wherein said universal transaction card comprises of a NFC smartcard with a magnetic stripe card emulation for storing users' payment and loyalty cards;
  v. wherein said application comprises of password protective logins and identification codes for preserving sensitive information and the capability to interface with the chip writer to program said universal card to provide information for a specific information exchange transaction; and
  vi. wherein said application further comprises a remote login from an alternate computing source to allow for access to said information exchange either by providing further account information or for disabling the ability to use or view the information should the system become lost or stolen.

16. The casing and exchange system of claim 15, wherein said universal card is demagnetized thus rendering the card unreadable after any of the following; a programmed number of uses; a set amount of time; or the application is prompted to lock-out further uses of the card until the card is reprogrammed.

17. The casing and exchange system of claim 16, wherein said programmed number of uses is after each single use.

18. The casing and exchange system of claim 16, wherein said set amount of time before the card is timed out rendering the card unusable until being reprogrammed is between 1 minute and 1 hour.

19. The casing and exchange system of claim 15, wherein the physical connection from said case to said phone is selected from one of the following connection possibilities: 30 point pin connection, USB, Micro USB, and audio jack.

20. The casing and exchange system of claim 15, wherein the physical connection from said case to said phone is through a 30 point pin connection.

* * * * *